United States Patent
Lenormand et al.

(10) Patent No.: US 7,082,812 B2
(45) Date of Patent: Aug. 1, 2006

(54) METHOD AND DEVICE FOR EVALUATING PHYSICAL PARAMETERS OF AN UNDERGROUND RESERVOIR FROM ROCK CUTTINGS TAKEN THEREFROM

(75) Inventors: Roland Lenormand, Rueil Malmaison (FR); Patrick Egermann, Rueil Malmaison (FR); Arnaud Templier, Colombes (FR)

(73) Assignee: Institut Francais du Petrole, Rueil-Malmaison Cedex (FR)

( * ) Notice: Subject to any disclaimer, the term of this patent is extended or adjusted under 35 U.S.C. 154(b) by 132 days.

(21) Appl. No.: 10/809,895

(22) Filed: Mar. 26, 2004

(65) Prior Publication Data

US 2004/0211252 A1    Oct. 28, 2004

(30) Foreign Application Priority Data

Mar. 26, 2003   (FR) .................................. 03 03742

(51) Int. Cl.
*G01N 15/08*    (2006.01)
(52) U.S. Cl. .......................................... 73/38
(58) Field of Classification Search ...................... 73/38
See application file for complete search history.

(56) References Cited

U.S. PATENT DOCUMENTS

| | | | |
|---|---|---|---|
| 4,253,327 A | | 3/1981 | Wiley |
| 4,699,002 A | * | 10/1987 | Rockley ................... 73/152.07 |
| 5,832,409 A | | 11/1998 | Ramakrishnan |
| 6,453,727 B1 | * | 9/2002 | Lenormand et al. ............ 73/38 |

| | | | |
|---|---|---|---|
| 6,935,159 B1 | * | 8/2005 | Knight et al. ................... 73/38 |

FOREIGN PATENT DOCUMENTS

EP    1167948    1/2002

* cited by examiner

*Primary Examiner*—Hezron Williams
*Assistant Examiner*—John Fitzgerald
(74) *Attorney, Agent, or Firm*—Antonelli, Terry, Stout and Kraus, LLP.

(57) ABSTRACT

Method and device for evaluating, simultaneously and with a single equipment, physical parameters such as the absolute permeability and the porosity of fragments taken from a fragmented artificial or natural porous medium.

The porosity of the fragments is measured by means of pressure tests using helium or any other gas, according to a protocol known in the art. Chamber (1) in which they are contained is communicated with a tank (11) of known volume containing helium at a known pressure. At pressure balance, the value of the solid volume can be deduced. The rock envelope volume and the mass in fragments are also measured. The porosity of the samples and the density of the rock are determined by combining these measurements. Their permeability is then measured by immersing them in a liquid and by communicating the chamber with a liquid initially at a predetermined pressure contained in an accumulator (9) so as to compress the gas trapped in the pores of the rock. The values of the physical parameters are determined by modelling the evolution of the volume of liquid injected in the chamber and by means of an iterative adjustment.

Applications: petrophysical measurements from drill cuttings or crushed cores for example.

14 Claims, 6 Drawing Sheets

METHOD AND DEVICE FOR EVALUATING PHYSICAL PARAMETERS OF AN UNDERGROUND RESERVOIR FROM ROCK CUTTINGS TAKEN THEREFROM

FIELD OF THE INVENTION

The present invention relates to a method and to experimental devices for evaluating, with a single equipment and simultaneously, the porosity and the absolute permeability of any fragmented natural or artificial more or less porous medium from rock samples taken from this medium. The samples can be for example rocks from a zone of an underground fluid reservoir (hydrocarbon reservoir, aquifer, etc.) or possibly rocks of very low permeability such as clays or shales. The fragments are for example obtained during well drilling operations: drill cuttings or fragments obtained by crushing bigger samples: cores or lateral cores taken in a well.

The current petroleum context leads operators to take an interest in new zones (deep offshore) and in new reservoir types (marginal structures located close to existing surface installations). Considering the drilling costs linked with the difficult environment of these new discoveries or with the limited size of certain structures, operators can no longer afford to drill complementary appraisal wells without risking compromising the economic viability of the project. The development strategy set before starting production is therefore less strict so as to allow <<real-time>> adaptation to the nature of the information collected by drilling production wells. This is referred to as appraisal development.

Petrophysical measurements have a key role in the assessment of the quality of a reservoir. However, the time required for this type of measurements is often very long and therefore incompatible with the reactivity necessary for the success of appraisal developments. New, faster and less expensive evaluation means are thus required as a support to decision-making.

Cuttings carried along by the drilling mud have been subjected to examinations in the field for a long time. They are carried out by the crews in charge of mud logging and they essentially help to complete the description of the geologic layers drilled, performed from logs.

BACKGROUND OF THE INVENTION

Work has already been done to try to evaluate petrophysical properties from drill cuttings. The acoustic properties as regards S and P waves (shear and compressional waves) have been measured for example. Various parameters have also been studied, such as the hardness and the deformation of the rock fragments, or their porosity and permeability.

According to a first known method intended for permeability measurement, the rock fragment is first coated with resin. A thin slice is cut out of the coated rock and placed in a measuring cell. It comprises means for injecting a fluid under pressure at a controlled flow rate and means for measuring the pressure drop created by the sample. Since the resin is impermeable, the absolute permeability is deduced from Darcy's equation by taking account of the real surface area occupied by the rock fragments.

This method is for example described by:
Santarelli F. J., et al.; <<Formation evaluation from logging on cuttings>>, SPERE, June 1998, or
Marsala A. F., et al.; <<Transient Method Implemented under Unsteady State Conditions for Low and Very Low Permeability Measurements on Cuttings>>, SPE/ISRM No.47202, Trondheim, 8–10 July 1998.

This type of measurement can only be obtained in the laboratory after long fragment conditioning operations.

Another well-known method is based on a NMR (Nuclear Magnetic Resonance) measurement which is directly carried out on the cuttings after prior washing followed by brine saturation. This type of measurement gives a porosity value that can be directly used. The permeability K is determined by means of correlations of the same nature as those used within the context of NMR logging.

An illustration of this method can be found in the following document:
Nigh E., et al.; P-K™: Wellsite Determination of Porosity and Permeability Using Drilling Cuttings, CWLS Journal, Vol.13, No.1, December 1984.

Patent application EP-1,167,948 and patent applications FR-02/02,242 and 03/00,429 describe several systems for evaluating physical parameters such as the absolute permeability of porous rocks from a zone of an underground reservoir, from rock fragments taken in this zone, such as rock fragments carried along by the drilling mud. It comprises a stage of immersing fragments contained in a containment chamber in a viscous fluid and of placing the chamber containing the fragments under pressure according to several implementation modes so as to compress the gas trapped in the pores of the rock.

According to an implementation mode, a fluid is injected at a pressure that increases with time, up to a predetermined pressure threshold, so as to compress the gas trapped in the pores of the rock. This injection stage is followed by a relaxation stage where injection is stopped. The pressure variation during these two successive stages is recorded.

According to another implementation mode, the chamber containing the fragments is communicated with a vessel containing a viscous fluid at a predetermined pressure. The communication stage being short, a fast pressure increase in the chamber and compression of the gas trapped in the pores of the rock are obtained, followed by a relaxation period after isolation of the chamber, and the pressure evolution in the chamber during the two periods is measured.

According to another implementation mode, the chamber containing the fragments is communicated with a vessel containing a viscous fluid at a predetermined constant pressure so as to cause a fast and prolonged pressure increase in the chamber and compression of the gas trapped in the pores of the rock, and the evolution of the volume of fluid injected is measured as a function of time.

Whatever the operating mode, the evolution of the pressure or of the volume of fluid injected having been modelled from initial values selected for the physical parameters of the fragments, the computer adjusts them iteratively so as to obtain the best possible match between the modelled pressure or volume curve and the pressure or volume curve really measured.

SUMMARY OF THE INVENTION

The object of the method according to the invention is to evaluate, with a single equipment, physical parameters such as the absolute permeability and the porosity of a fragmented natural or artificial porous medium from rock fragments taken in this medium. It comprises a stage of immersing fragments contained in a containment chamber in a (more or less viscous) liquid and of intermittently communicating the chamber containing the fragments with a source of liquid under pressure comprising an accumulator containing an elastic volume of liquid so as to compress the gas trapped in the pores of the rock, a stage of measuring the volume of liquid injected, a stage of modelling the evolution of the volume of liquid injected from a priori selected initial values at least for the permeability and the residual gas saturation, and a stage of iterative adjustment of the value of the physical parameters of the rock fragments so as to obtain the best possible adjustment of the modelled evolution of the volume injected with the measured evolution of the volume injected in the chamber.

The method is characterized in that, during the stage of immersing in the liquid the fragments contained in the containment chamber, the volume of liquid injected is measured by measuring the concomitant variation of the pressure prevailing in said accumulator.

The modelling stage can also be carried out from a priori selected initial porosity values. It can also comprise a prior stage of feeding the washed and dried rock fragments into the containment chamber which is first communicated with a gas tank at a predetermined pressure, so as to determine the solid volume of said fragments, with measurement of the envelope volume and of the mass of the fragments so as to deduce the porosity and the density of the rock fragments. In this case, the modelling stage comprises modelling the evolution of the volume of liquid injected from a priori selected initial permeability and residual gas saturation values, and from the value previously measured for the porosity.

According to an implementation mode, the stage of communicating the chamber with the accumulator is carried out so as to cause a fast pressure increase in the chamber and compression of the gas trapped in the pores of the rock, followed by a relaxation period after isolation of the chamber, and it comprises measuring the evolution of the pressure in the chamber during these two successive stages.

The containment chamber can for example be filled with drill cuttings, rock fragments obtained by crushing cores taken in a well, notably cores obtained by sidewall coring of a well, rock fragments invaded by drilling fluids, previously cleaned rock fragments, etc.

The device according to the invention allows to evaluate physical parameters such as the absolute permeability and the porosity of a fragmented artificial or natural porous medium such as a zone of an underground reservoir, from fragments taken from this medium, comprising a processing system, a containment chamber for the fragments, an injection assembly for injecting a liquid into the chamber so as to fill the chamber containing the rock fragments, and for carrying out a cycle comprising a stage of liquid injection into the chamber, this assembly comprising an accumulator containing an elastic volume of liquid and means controlled by the processing system for controlling communication of the accumulator with the chamber containing the rock fragments. Means are used to measure the pressure in the chamber. The processing system is suited for modelling the evolution of the volume of liquid injected from initial values selected for the physical parameters of the rock fragments, and for adjusting iteratively the values to be given to these physical parameters so as to obtain the best possible adjustment between the modelled evolution of the physical quantity and the measured evolution of said quantity in the chamber.

The device is characterized in that it comprises means for measuring pressure variations in the accumulator and in that the processing system is suited for computing the volume of liquid injected in the chamber from the accumulator, from the pressure variation measured by the pressure measuring means.

The device comprises for example a gas tank that can be communicated with the chamber by means of a valve, a means for measuring the volume envelope (such as a powder pycnometer for example) for determination of the porosity of the fragments and a means for measuring the mass of the fragments.

The elastic volume of liquid is for example delimited in the accumulator by either a gas volume, in which case the relation is obtained by applying the gas law, or by an elastic membrane or any other moving element, in which case the relation is obtained by prior calibration of the deformations or displacements.

The method proves to be satisfactory for very varied rocks within a wide permeability and porosity range. It is very accurate because the measurement of the volume of liquid injected is not obtained directly as in the aforementioned patent applications but indirectly by measuring the pressure variations in the accumulator, which can be readily done with high precision.

Considering the limited space occupied by the device, its ease of use and the rapidity with which the measurements and the adjustment between the theoretical data and the experimental data can be performed, the method is particularly well-suited for field conditions. It is therefore possible to carry out measurements and interpretations directly in the field in a very short time, which consequently has nothing in common with the time required to obtain equivalent results by means of laboratory methods. This opens up interesting prospects for petrophysical characterization in the petroleum and hydrologic sphere: permeability evolution, porosity, rock density, etc., since it is possible to take advantage of this new source of information as a support for the interpretation of electric logs and to fine down the evaluation of a well in terms of production potential. This also opens up important prospects for the petrophysical characterization of any other fragmented natural or artificial porous medium.

BRIEF DESCRIPTION OF THE FIGURES

Other features and advantages of the method and of the device according to the invention will be clear from reading the description hereafter of embodiments given by way of non limitative example, with reference to the accompanying drawings wherein.

DETAILED DESCRIPTION

Figure 1:
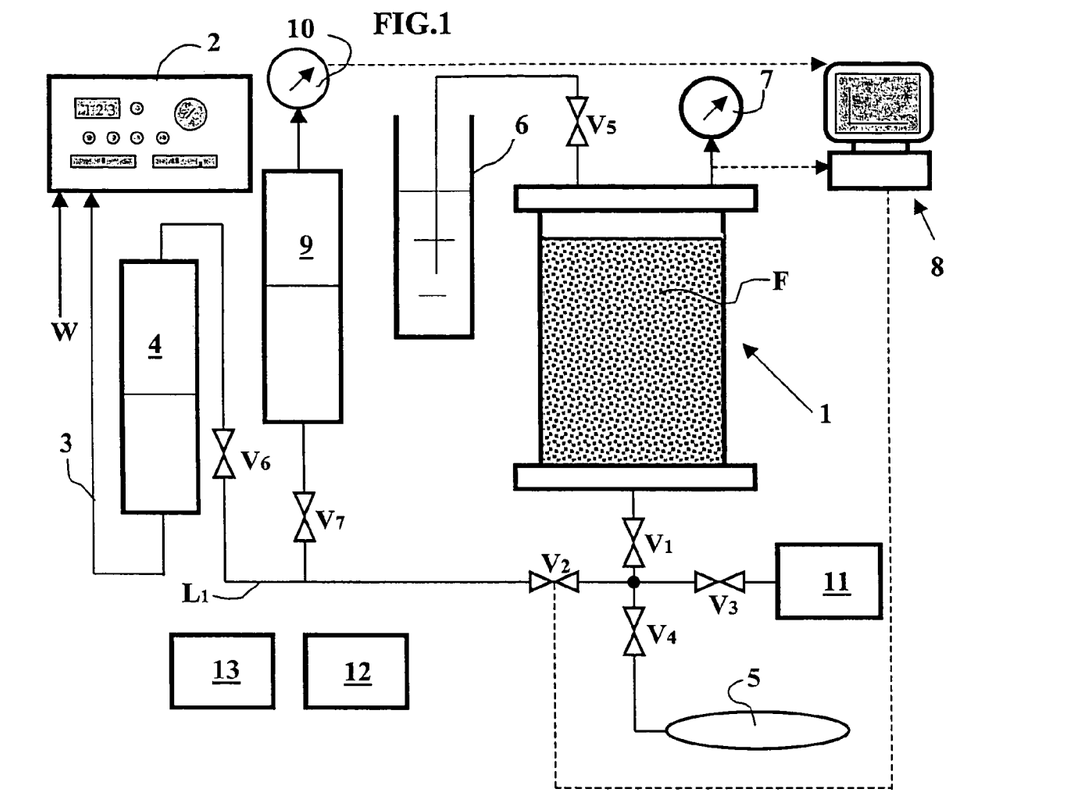
FIG. 1 diagrammatically shows the device.

The device diagrammatically shown in FIG. 1 comprises a containment chamber 1 in which the drill cuttings are initially placed. An injection system 2 communicates through a line 3 with the base of a surge tank 4 containing a more or less viscous liquid suited to the permeability to be measured, such as oil. The opposite end of surge tank 4 communicates through a valve V6 with a line L1. A first end of containment chamber 1 communicates with line L1 through the agency of two valves V1, V2. The opposite end of containment chamber 1 communicates, by means of an isolating valve V5, with a separator 6. A manometer 7 is connected to the outlet of chamber 1. The pressure variations measured by manometer 7 are acquired by a processor 8 such as a microcomputer. Valve V2 is directly controlled by processor 8. Line L1 also communicates by means of a valve V7 with an accumulator 9 containing a more or less viscous liquid, placed under a predetermined pressure by a gas cap under pressure, a flexible membrane or a moveable element. A manometer 10 is connected to the outlet of accumulator 9. The pressure variations measured thereby are also acquired by processor 8.

Fragments available after cleaning, from which all the fluids have been previously removed, can also be used. In cases where containment chamber 1 is filled with cleaned fragments, a gas such as helium for example, coming from a bottle 5, can be injected by opening a valve V4 so as to expel the air from the chamber.

Chamber 1 is also connected, by means of valves V1 and V3, to a tank 11 filled with helium and whose volume is known. Chamber 1 can be communicated with tank 11 initially at a known pressure by opening V1 or V3, valves V2 and V4 being closed.

The device further comprises a balance 12 and a powder pycnometer type instrument 13 allowing to measure the envelope volume of the fragments introduced.

I) Porosity Measurement

Determination of the porosity comprises a stage of acquisition of experimental measurements of the envelope volume Ve of the fragments introduced, of the solid volume Vs of rock introduced and of the mass $m_e$ of rock introduced, and a stage of calculation of the porosity and of the density of the rock.

a) Measurement Acquisition

The cleaned and dried fragments are previously weighed on balance 12 and their envelope volume is measured by means of instrument 13. The fragments are then fed into containment chamber 1 placed under gaseous atmosphere (helium for example) through communication with tank 5 so as to expel the air. Chamber 1 is then connected to tank 11 filled with helium and of known volume by opening valves V1 and V3, valves V2 and V4 being closed. The balance pressure allows to deduce the value of the solid volume of the rock from the initial pressures in chamber 1 and tank 11 and from their volumes. All these measurements allow to determine the porosity of the samples. The density of the rock is also obtained by measuring the mass of the fragments introduced.

Envelope volume Ve is obtained by means of a powder pycnometer according to a technique known to specialists.

Let P1 be the initial pressure in 1, Ph the initial pressure in tank 11, Pe the balance pressure after communication, U1 the volume of chamber 1, Vh the volume of tank 11 and mc the mass of the fragments used.

Vs, φ and d are respectively the solid volume, the porosity and the density of the rock. We have:

$$Vs = U1 - Vh\frac{(Ph - Pe)}{(Pe - P1)}$$

$$\phi = \frac{Ve - Vs}{Ve}$$

$$d\text{rock} = \frac{mc}{Ve}.$$

FIG. 11 shows that a very good estimation of the porosity of the rocks tested is obtained.

II) Permeability Estimation

Estimation of the absolute permeability essentially comprises three stages:

1) a stage of acquisition of experimental measurements of the pressure variations (or of the evolution of the volume injected) from the drilling fragments, which leads to experimental curves, 2) a stage of modelling the physical phenomena occurring in the drilling fragments during the same operating cycle, for arbitrary values of physical parameters sought (permeability K and porosity φ) involved in the model, allowing to establish similar theoretical curves, and 3) an adjustment or calibration stage wherein the values to be given to the physical parameters involved in the model are determined so as to obtain the best possible adjustment between the experimental curves and the theoretical curves.

1) Measurement Acquisition

Chamber 1 is filled with a more or less viscous liquid (with a viscosity suited to the permeability to be measured: oil for example, glycerol, water, any aqueous, viscous solution, etc.) or by means of the injection system. The liquid occupies the free space between the drilling fragments and it also flows, by spontaneous imbibition, into the rock. A liberation of gas whose intensity and duration depend on the nature of the rock (mainly the porosity) takes place. This gas liberation only involves part of the gas. A certain residual volume remains trapped in the drilling fragments in form of disconnected pockets.

The procedure essentially consists in communicating chamber 1, which contains rock fragments C, with accumulator 9 which contains liquid under pressure (Pini) by opening valve V2 controlled by control processor 8.

Initially, the valve is closed. On the side of accumulator 9, the pressure is Pini, whereas on the side of chamber 1, the pressure is equal to the ambient pressure. Valve V2 controlled by processor 8 is then opened for some tenths of a second so as to rapidly increase the pressure in chamber 1 up to Pmax. The elasticity of the volume of accumulator 9, obtained by means of a gas cap, of a flexible membrane that deforms under the effect of a pressure change or of a moveable element, is previously calibrated so as to measure a pressure decrease of some bars in accumulator 9 during the test. This pressure change then allows to readily calculate the evolution of the volume of liquid injected from accumulator 9 into chamber 1 from the gas law (if a gas cap is used) or from a calibration curve (if a flexible membrane or a moveable element is used).

In relation to the procedures described in the aforementioned patent applications, this approach allows to simplify the course of the experiment (no flowmeter or differential detector to be inserted as previously on line LI connecting the accumulator to the chamber to measure the volume injected) while keeping good control of the volume injected, which facilitates acquisition of the measurements and interpretation of the results with the simulator. Besides, elimination of a flowmeter or of a differential detector for measuring the volume injected allows:

to greatly miniaturize the dimensions of the measuring instrument, so that a measurement can be performed with only 1 cm$^3$ of fragment, to shorten the connecting lines between accumulator 9 and chamber 1, which shortens the time during which the chamber containing the fragments is placed under pressure and improves the sensitivity of the instrument. It is thus possible to test rocks having an average diameter of the order of 1 mm for permeabilities up to several hundred milliDarcy, to measure very small variations of the volume injected (less than 0.03 cm$^3$ of cumulative liquid injected), which was difficult to do with a flowmeter or a differential detector, to operate the measuring instrument with liquids of different viscosities without having to adapt the system for measuring the volume injected, which greatly improves the flexibility of the instrument.

Figure 3A:
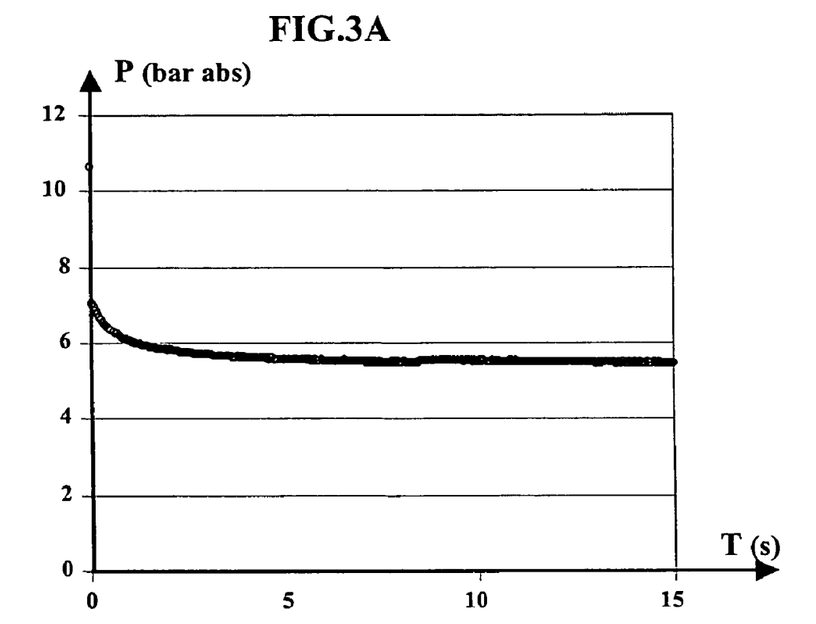
FIGS. 3A and 3B show a pressure evolution measured during a test with the corresponding evolution of the volume of liquid injected as a function of time calculated from the gas law, FIGS. 4A to 4C diagrammatically show the curves of the volume of liquid injected as a function of time obtained from the pressure evolution in the chamber of the device of FIG. 1 for three different rocks.
Figure 3B:
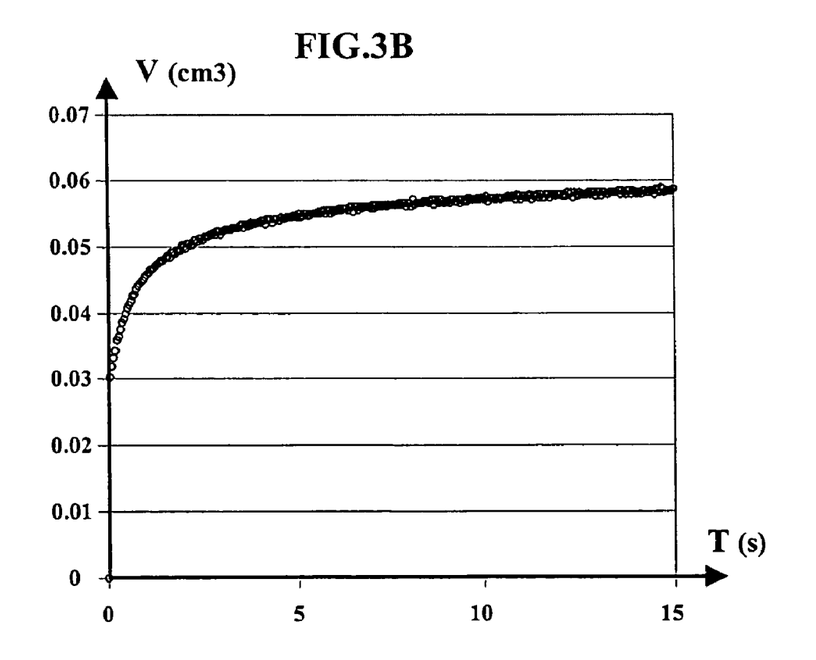
Figure 4A:
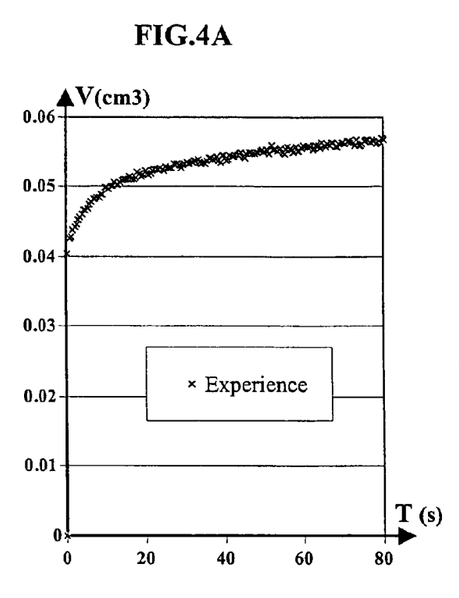
Figure 4B:
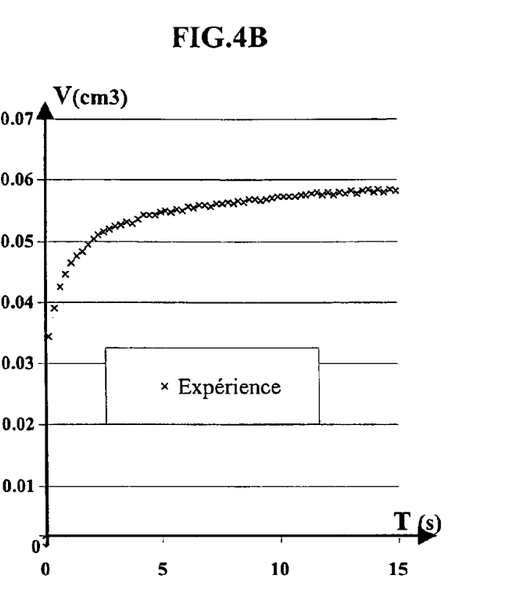
Figure 4C:
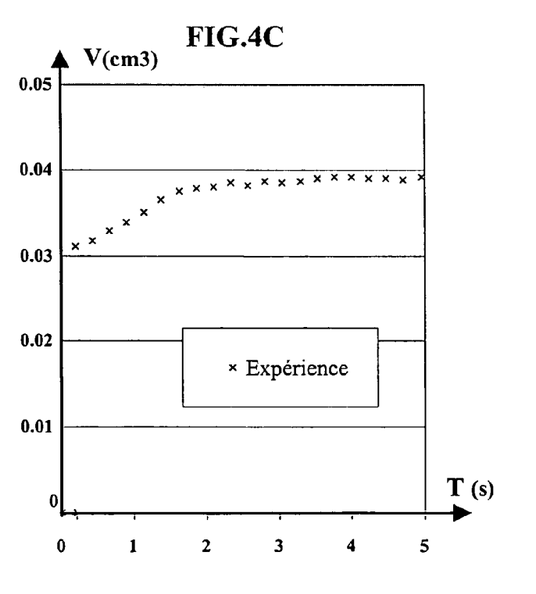

FIGS. 3A to 3C show examples of injected volume curves as a function of time for three different rocks. Significant variations of the filling curves are observed according to the nature of the rocks tested. The lower the permeability of the rocks, the slower the filling kinetics (more than 80 seconds for the least permeable rock shown, FIG. 4A, and less than 2 seconds for the most permeable rock shown, FIG. 4C).

The goal of the next two stages is to obtain, from the pressure or injected liquid volume measurements, an estimation of permeability K alone (if the porosity has been measured before as described above) or a combined estimation of permeability K and of porosity ($\phi$)

2) Modelling

The drill cuttings are considered to be of homogeneous size and of spherical shape, and the gas is assumed to be perfect. The pressure drop due to the viscosity of the gas is disregarded in relation to that of the liquid, considering the difference between the viscosities. The residual gas trapped in the rock fragments after spontaneous imbibition of the liquid has the form of disconnected homogeneously distributed pockets. The capillary pressure is also considered to be negligible.

Considering the spherical shape of the fragments, we will consider a cap of thickness dr (FIG. 2) and calculate the evolution of the pressure at the boundary of the rock particle when a flow of liquid q is injected.

Figure 2:
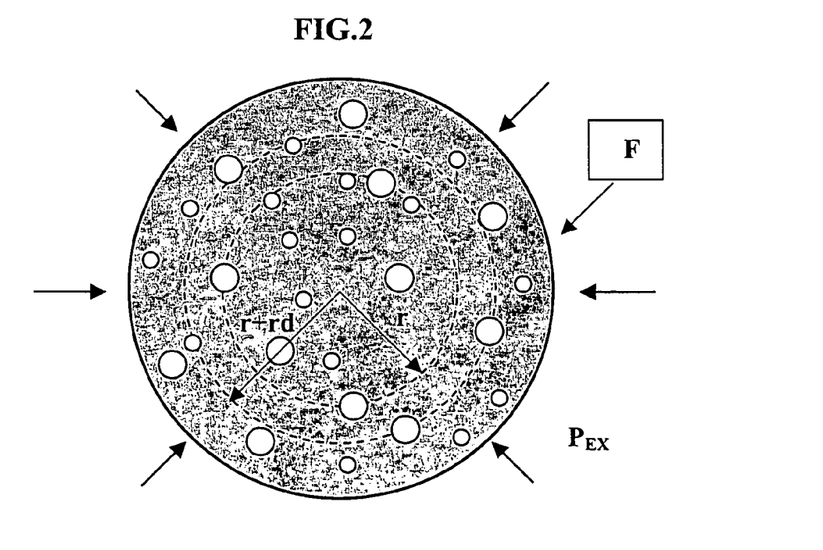
FIG. 2 diagrammatically shows the structure of a fragment or particle of a porous rock wherein the effects of the injection of a high-viscosity liquid such as oil are modelled.

We consider that the total flow rate Q of the liquid injected is equitably divided among the N rock particles and that each one receives the flow rate $$q = \frac{Q}{N}.$$

The gas law allows to deduce the local gas saturation Sg from the moment that the pressure $$P \cdot S_g = S_{g0} \frac{P_0}{P}$$

($P_0$ is the pressure of the liquid) is known. In the cap, a material balance is performed on the liquid. The accumulation is equal to the difference between what goes in and what goes out. We deduce therefrom that:

$$\mathrm{div}\vec{V}_0 + \phi \frac{\partial S_0}{\partial t} = 0.$$

Since $S_0 = (1 - S_g) = \left(1 - S_{g0}\frac{P_0}{P}\right)$, we deduce that:

$$\frac{\partial S_0}{\partial t} = \frac{\partial S_0}{\partial P}\frac{\partial P}{\partial t} = \left(S_{g0}\frac{P_0}{P^2}\right)\frac{\partial P}{\partial t}$$

Besides, since $$\vec{V}_0 = -\frac{K}{\mu_0}\mathrm{grad}P_0$$

(K is the permeability and $\mu_0$ the viscosity of the liquid), and since the capillary pressure can be considered to be negligible, so that we have $P_0 = P_{gas} = P$, the previous equation can be written in the following form:

$$-\frac{K}{\mu_0}\Delta P + \phi S_{g0}\frac{P_0}{P^2}\frac{\partial P}{\partial t} = 0.$$

It follows therefrom that $$\Delta P = \frac{\mu_0 \phi S_{g0}}{K}\frac{P_0}{P^2}\frac{\partial P}{\partial t}.$$

We therefore obtain the conventional form of a diffusion type equation with, however, a $1/p^2$ term factor of the accumulation due to the compressible nature of the gas.

In spherical coordinates, the Laplacian is $$\frac{1}{r^2}\frac{\partial}{\partial r}\left(r^2\frac{\partial P}{\partial r}\right).$$

Finally, the equation to be solved is written as follows:

$$\frac{\partial}{\partial r}\left(r^2\frac{\partial P}{\partial r}\right) = \alpha\frac{r^2}{P^2}\frac{\partial P}{\partial t} \quad (1)$$

$$\text{with } \alpha = \frac{\mu_0 \phi S_{g0} P_0}{K}. \quad (2)$$

As it is injected, the liquid expels the air in the free space between the drilling fragments and it enters the rock by spontaneous imbibition. Despite certain precautions, a certain volume of gas may remain outside because of the non-regular shape of the drill cuttings. This trapped volume ($V_{gp}$) plays a direct part in the general form of the pressure response and it has to be taken into account in the solution.

A certain compressibility due to the experimental device also has to be taken into account. It comes from the chamber, from the lines as well as from the properties of the liquid. The equivalent compressibility observed is of the order of 0.0005 bar$^{-1}$ (50 Pa).

As the liquid used is saturated with gas at atmospheric pressure, dissolution phenomena occur when the pressure rises during measurement. These aspects are taken into account by introducing a diffusion parameter representative of the molecule exchanges at the level of the gas/liquid interfaces.

The diffusion equation is solved by means of the finite-difference method with an explicit scheme and by applying the boundary conditions in time $P(r,0)=P_{atm}$ and in space $P(R,t)=P_{ext}$, and $$\frac{\partial P}{\partial r}(0,t) = 0.$$

Within the context of the experimental procedure described above, the pressure evolution in the chamber containing the fragments, i.e. Pext, is directly measured. It is thus possible to directly solve the equation governing the evolution of the pressure in the rock explicitly. The evolution of the simulated volume of liquid injected as a function of time is then calculated by difference between the volume of gas initially present in the rock (at Patm) and the volume occupied by the gas at a time t during the test (during the compression stage).

3) Adjustment of the Model to the Experimental Results

The model is implemented in a calculator such as computer 8 (see FIG. 1) in form of a software and it is inserted in an iterative optimization loop. The model is operated with a priori selected permeability K and residual gas saturation values, by imposing for porosity ($\Phi$) the value obtained experimentally, and the resulting simulated injected volume curve is compared with the experimental curve, by successive iterations, by changing the values of K and of the residual gas saturation in the model. The values that allow the best possible adjustment of the theoretical and experimental curves are found through the agency of a conventional Newtonian or gradient type optimization method.

In cases where porosity ($\Phi$) has not been previously measured experimentally, the model is operated with a priori selected permeability K, residual gas saturation and porosity values, and the resulting simulated injected volume curve is compared with the experimental curve, by successive iterations, by changing the values of K, of porosity $\Phi$ and of the residual gas saturation in the model. FIG. 11 shows that a satisfactory estimation of the porosity of the rocks tested is obtained.

When the value of the previously measured porosity is known, only the permeability value K has to be adjusted in the modelling stage. The modelling operation is therefore faster. It is also more accurate, as can be clearly seen in FIG. 12.

Figure 5:
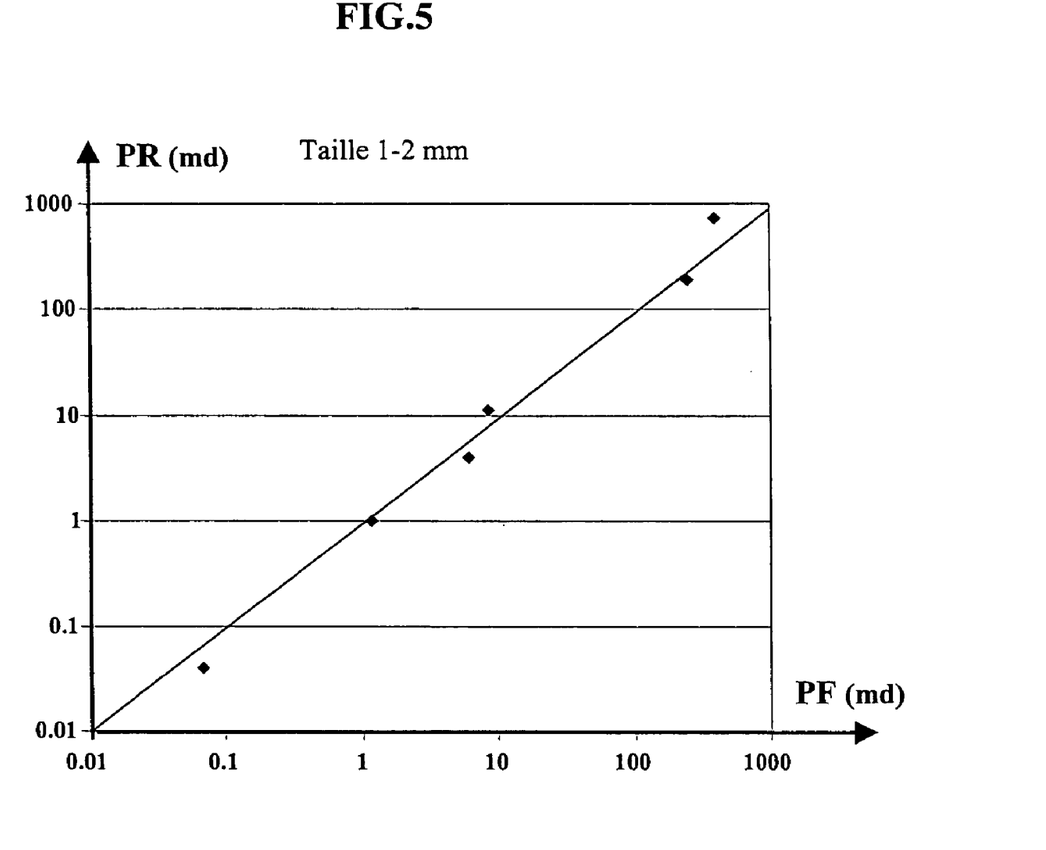
FIG. 5 shows the good match between the permeabilities obtained for several rock types by means of a conventional core measuring method and by means of the method according to the invention.
Figure 6A:
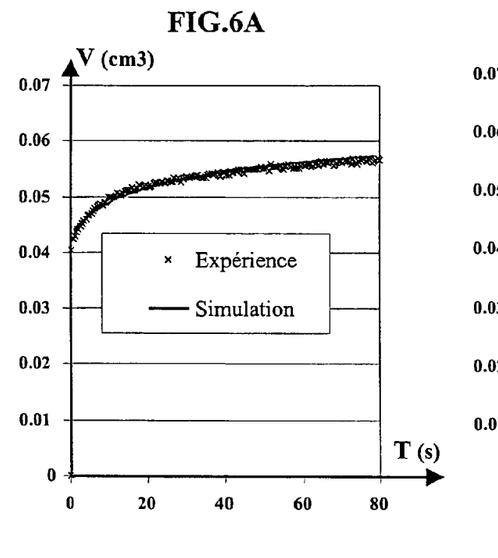
FIGS. 6A to 6C show, for the previous three rocks, the accuracy obtained in the adjustment of the modelled injected volume curves in relation to the experimental curves.
Figure 6B:
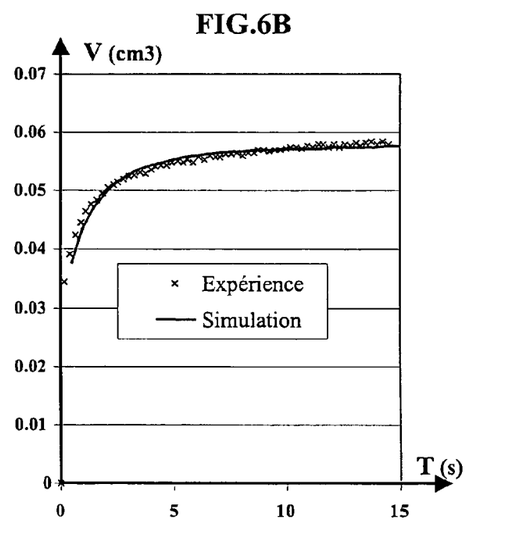
Figure 6C:
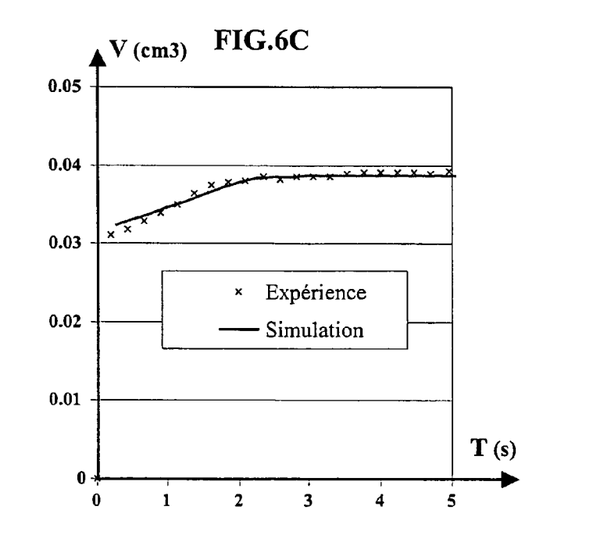
Figure 7:
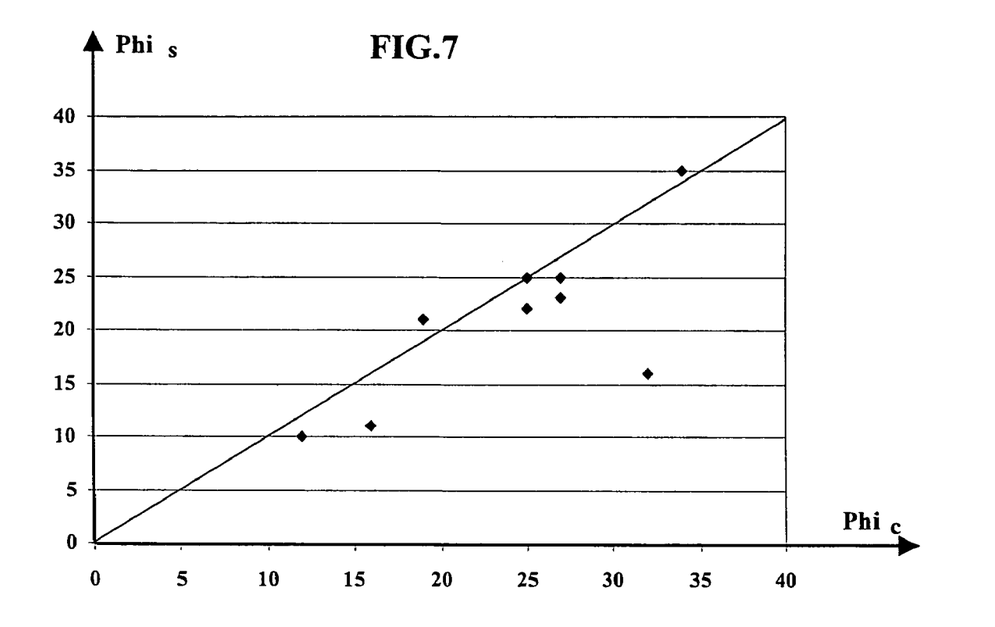
FIG. 7 shows the good match obtained between the values of the porosity (Φ or $Phi_c$) of the rock fragments tested and those ($Phi_s$) obtained for samples or cores in cases where the a priori porosity and permeability values are iteratively adjusted.
Figure 8:
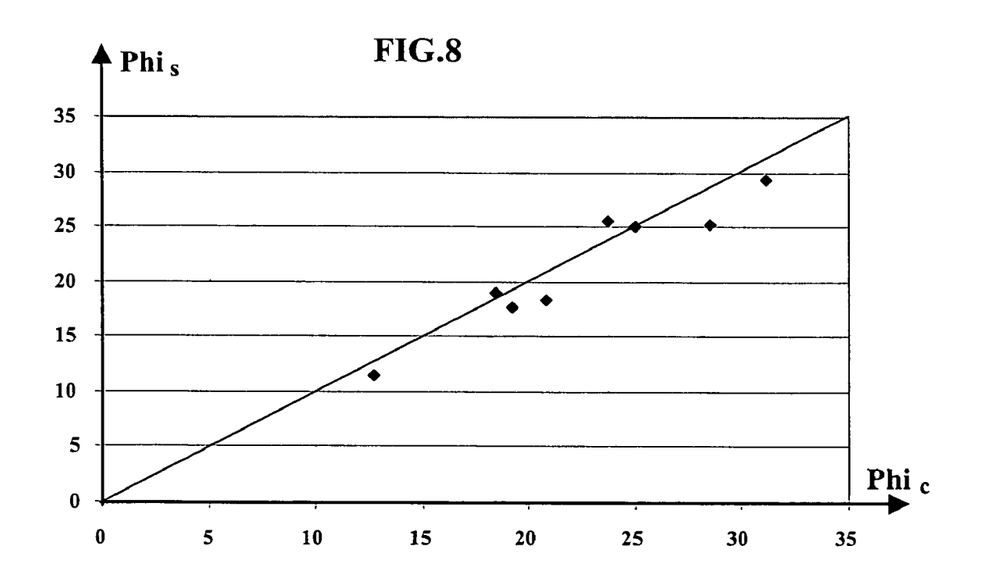
FIG. 8 shows the result of the porosity determination of the rock fragments tested when the porosity ($Phi_c$) of the fragments is first measured experimentally.

FIGS. 6A to 6C show the comparison obtained by successive iterations between the theoretical and experimental curves for three rock types tested. In any case, a very good match is observed between the simulations and the experimental results. The results obtained by applying the method are quite comparable to those obtained in the laboratory after long conditioning periods using conventional methods for several rocks of different permeabilities as shown in FIG. 5.

Programming this modelling within a code allows to calibrate the experiments by means of an optimization loop, which allows the corresponding value of K to be rapidly deduced.

The invention claimed is:

1. A method for evaluating, with a single equipment, physical parameters of a fragmented porous medium from rock fragments taken in this medium, comprising a stage of immersing fragments contained in a containment chamber in a liquid and of intermittently communicating the chamber containing the fragments with a source of liquid under pressure comprising an accumulator containing an elastic volume of liquid, so as to compress the gas trapped in the pores of the rock, a stage of measuring the volume of liquid injected, a stage of modelling the evolution of the volume of liquid injected from a priori selected initial values at least for permeability and the residual gas saturation, and a stage of iterative adjustment of the value of the physical parameters of the rock fragments so as to obtain the best possible adjustment of the modelled evolution of the volume injected with the measured evolution of the volume injected in the chamber, characterized in that:

during the stage of immersion, in the liquid, of the fragments contained in the containment chamber, the volume of liquid injected is measured by measuring the concomitant pressure variation in said accumulator.

2. A method as claimed in claim 1, wherein the modelling stage is also carried out from a priori selected initial values for porosity.

3. A method as claimed in claim 1, comprising a prior stage of feeding the washed and dried rock fragments into containment chamber which is first communicated with a gas tank at a predetermined pressure, so as to determine the solid volume of said fragments, the envelope volume and the mass of the fragments are measured, and the porosity and the density of the rock fragments are deduced therefrom, the modelling stage comprising modelling the evolution of the volume of liquid injected from a priori selected initial values of permeability and of the residual gas saturation, and from the value measured for porosity.

4. A method as claimed in claim 1, wherein the stage of communicating the chamber with the accumulator is carried out so as to cause, during a first period, a fast pressure increase in the chamber and compression of the gas trapped in the pores of the rock, followed by a relaxation period after isolation of the chamber, and comprises measuring the evolution of the pressure in the chamber during the two periods.

5. A method as claimed in claim 1, wherein the containment chamber is filled with drill cuttings.

6. A method as claimed in claim 1, wherein the containment chamber is filled with rock fragments obtained by crushing cores taken in a well, notably cores obtained by sidewall coring of a well.

7. A method as claimed in claim 1, wherein the containment chamber is filled with rock fragments invaded by drilling fluids.

8. A method as claimed in claim 1, wherein the containment chamber is filled with previously cleaned rock fragments.

9. A device for evaluating physical parameters of a fragmented porous medium from fragments taken in this medium, comprising a processing system, a containment chamber for the fragments, an injection assembly for injecting a liquid into the chamber so as to fill the chamber containing the rock fragments, and for carrying out a cycle comprising a stage of liquid injection into the chamber, this assembly comprising an accumulator containing an elastic volume of liquid and means controlled by the processing system for controlling communication of the accumulator with the chamber containing the rock fragments, means for measuring the pressure in the chamber, the processing system being suited for modelling the evolution of the volume of liquid injected from initial values selected for the physical parameters of the rock fragments, and for adjusting iteratively the values to be given to these physical parameters so as to obtain the best possible adjustment between the modelled evolution of the physical quantity and the measured evolution of said quantity in the chamber, characterized in that it comprises pressure measuring means for measuring pressure variations in the accumulator and in that the processing system is suited for calculation of the volume of liquid injected in the chamber from the accumulator, from the pressure variation measured by the pressure measuring means.

10. A device as claimed in claim 9, comprising a gas tank that can be communicated with chamber by means of a valve, an instrument for measuring the envelope volume so as to determine the porosity of the fragments and means for measuring the mass of the fragments.

11. A device as claimed in claim 10, characterized in that the means for measuring the envelope volume of the fragments to be tested comprise a powder pycnometer.

12. A device as claimed in claim 10, wherein the elastic volume of liquid is delimited in said accumulator by a volume of gas, said relation being obtained by applying the gas law.

13. A device as claimed in claim 10, wherein the elastic volume of liquid is delimited in said accumulator by an elastic membrane or a moveable element, said relation being obtained by prior calibration of the deformations or of the displacements.

14. A device as claimed in claim 10, wherein the pressure measuring means for measuring pressure variations in the accumulator comprises a manometer connected to an outlet of the accumulator.

* * * * *